(12) United States Patent
Bauer et al.

(10) Patent No.: US 8,409,108 B2
(45) Date of Patent: Apr. 2, 2013

(54) MULTI-AXIAL HEART SOUNDS AND MURMUR DETECTION FOR HEMODYNAMIC-CONDITION ASSESSMENT

(75) Inventors: Peter T. Bauer, West Linn, OR (US); Marco Dalla Gasperina, Vancouver, WA (US); Patricia A. Arand, McMinnville, OR (US); Timothy K. Wheeler, Portland, OR (US)

(73) Assignee: Inovise Medical, Inc., Beaverton, OR (US)

( * ) Notice: Subject to any disclaimer, the term of this patent is extended or adjusted under 35 U.S.C. 154(b) by 202 days.

(21) Appl. No.: 12/940,433

(22) Filed: Nov. 5, 2010

(65) Prior Publication Data

US 2011/0105932 A1 May 5, 2011

Related U.S. Application Data

(60) Provisional application No. 61/280,558, filed on Nov. 5, 2009.

(51) Int. Cl.
*A61B 5/02* (2006.01)
(52) U.S. Cl. .................................................. 600/528
(58) Field of Classification Search .............. 600/493, 600/513, 514, 528
See application file for complete search history.

(56) References Cited

U.S. PATENT DOCUMENTS

| | | | |
|---|---|---|---|
| 5,392,780 A | 2/1995 | Ogino et al. |
| 5,758,654 A | 6/1998 | Burton-Krahn et al. |
| 7,039,538 B2 | 5/2006 | Baker, Jr. |
| 7,074,195 B2 | 7/2006 | Nelson et al. |
| 7,096,060 B2 | 8/2006 | Arand et al. |
| 7,113,820 B2 | 9/2006 | Schlegel et al. |
| 7,171,269 B1 | 1/2007 | Addison et al. |
| 7,174,203 B2 | 2/2007 | Arand et al. |
| 7,225,021 B1 | 5/2007 | Park et al. |
| 7,302,290 B2 | 11/2007 | Bauer |
| 7,424,321 B2 | 9/2008 | Wariar et al. |
| 7,431,699 B2 | 10/2008 | Siejko et al. |
| 7,559,903 B2 | 7/2009 | Moussavi et al. |
| 7,819,814 B2 | 10/2010 | Gavriely et al. |
| 8,105,241 B2 | 1/2012 | Nelson et al. |
| 8,137,283 B2 | 3/2012 | Syeda-Mahmood et al. |
| 2002/0188329 A1 | 12/2002 | Struble |
| 2003/0187337 A1 | 10/2003 | Tarassenko et al. |
| 2004/0127792 A1 | 7/2004 | Siejko et al. |
| 2004/0230105 A1 | 11/2004 | Geva et al. |
| 2005/0027323 A1 | 2/2005 | Mulligan et al. |
| 2005/0222515 A1 | 10/2005 | Polyshchuk et al. |
| 2006/0155202 A1 | 7/2006 | Arand et al. |
| 2007/0038137 A1 | 2/2007 | Arand et al. |

(Continued)

FOREIGN PATENT DOCUMENTS

CA 1256507 6/1989

OTHER PUBLICATIONS

USPTO Office Action for U.S. Appl. No. 12/321,646 dated Jun. 17, 2011. 9pp.

(Continued)

*Primary Examiner* — Brian T Gedeon
(74) *Attorney, Agent, or Firm* — Jon M. Dickinson, Esq.; Robert D. Varitz, Esq.

(57) ABSTRACT

A vector method for monitoring a subject's hemodynamic condition including (a) utilizing at least one, external or internal, anatomy-attached, three-axis accelerometer, collecting from the subject, during a selected cardiac cycle, related, three-orthogonal-axes accelerometer signal data, (b) following such collecting, processing collected signal data to obtain associated, signal vector, magnitude and directionality information, and (c) analyzing such obtained vector information for assessment of the subject's heart hemodynamic condition. ECG and signal time-frequency data is also collected and used in certain manners and implementations of the invention.

10 Claims, 3 Drawing Sheets

U.S. PATENT DOCUMENTS

Figure 1:
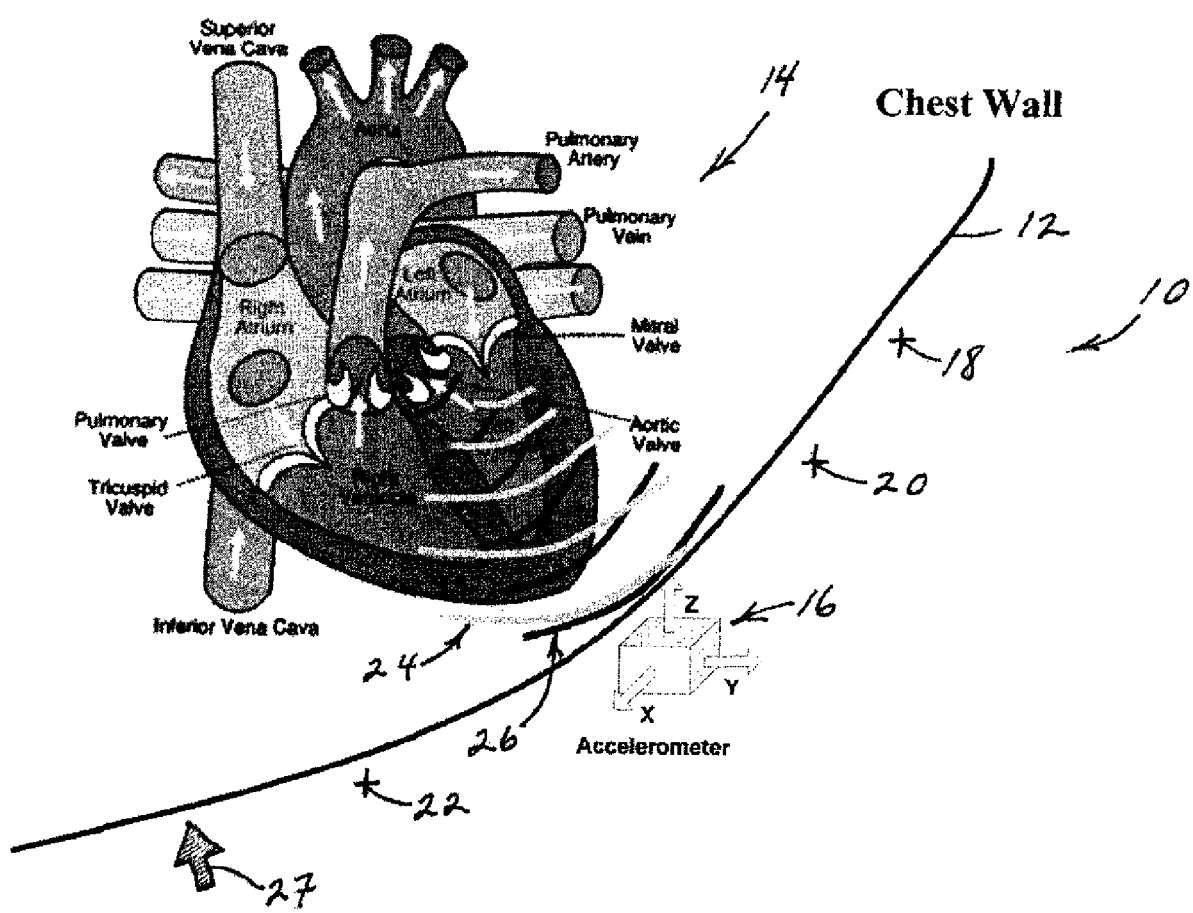

| | | |
|---|---|---|
| 2007/0055151 A1 | 3/2007 | Shertukde et al. |
| 2007/0191725 A1 | 8/2007 | Nelson |
| 2008/0021510 A1 | 1/2008 | Mi et al. |
| 2008/0177191 A1 | 7/2008 | Patangay et al. |
| 2008/0255465 A1 | 10/2008 | Nelson |
| 2009/0112107 A1 | 4/2009 | Nelson et al. |
| 2009/0112108 A1 | 4/2009 | Nelson et al. |
| 2009/0165559 A1 | 7/2009 | Lec |
| 2010/0094148 A1 | 4/2010 | Bauer et al. |

OTHER PUBLICATIONS

USPTO Office Action for U.S. Appl. No. 12/288,712 dated Apr. 11, 2011. 5pp.

USPTO Office Action for U.S. Appl. No. 12/321,647 dated Jun. 1, 2011. 7pp.

USPTO Office Action for U.S. Appl. No. 12/321,650 dated Sep. 7, 2011. 8 pp.

USPTO Office Action for U.S. Appl. No. 12/005,555 dated Dec. 23, 2010. 7pp.

International Search Report, Serial No. PCT/US10/055696, dated Dec. 23, 2010, 13 pages total.

USPTO Office Action, U.S. Appl. No. 12/315,165, dated Nov. 12, 2010, 9 pages total.

USPTO Office Action, U.S. Appl. No. 11/264,328, dated May 9, 2008, 7 pages total.

USPTO Office Action, U.S. Appl. No. 11/264,328, dated Oct. 16, 2008, 8 pages total.

MULTI-AXIAL HEART SOUNDS AND MURMUR DETECTION FOR HEMODYNAMIC-CONDITION ASSESSMENT

CROSS REFERENCE TO RELATED APPLICATION

This application claims filing-date priority to currently copending U.S. Provisional Patent Application Ser. No. 61/280,558, filed Nov. 5, 2009, for "Detection and Differentiation of Sleep Disordered Breathing Patterns". The entire disclosure content of this prior-filed provisional application is hereby incorporated herein by reference.

BACKGROUND AND SUMMARY OF THE INVENTION

This invention pertains generally to enhancing the assessment of a subject's hemodynamic condition via a newly proposed, non-invasive, three-dimensional, vector method for monitoring this condition. More particularly, it relates to a vector method, and to an associated, computer-based systemic setting appropriately provided for implementing this method, for monitoring a subject's hemodynamic condition utilizing sound-based information detected exclusively by an externally anatomically-attached, stably positioned, three-orthogonal-axis accelerometer in steps, broadly stated, which feature (a) attaching a three-orthogonal-axis accelerometer in a stable position externally to a subject's anatomy, (b) during at least one cardiac cycle of the subject, collecting signal data from the so attached accelerometer, (c) processing such collected data to obtain associated vector magnitude and directionality information, and (d) analyzing such vector magnitude and directionality information for assessment of the sought, subject's hemodynamic condition. As is pointed out below, where enhanced data-collection accuracy is desired, particularly in relation to the matter of heart murmur, plural, three-orthogonal-axis accelerometers are employed, placed in appropriate, spaced, stable, positions externally to a subject's anatomy.

The steps of this method will normally be practiced, aided by a suitably programmed, alliance, digital computer, by (or under the direct control of) a skilled medical clinician, beginning with the "attaching" step, and concluding with the combined "analyzing" and "assessing" step—this latter, combined step being performable in conjunction with the analytical knowledge possessed by such a clinician, aided in whole or in part by such a computer. Much of the process of such analyzing and assessing, beyond the important provision (by practice of the invention) of time-marked, vector-established, frequency-filtered magnitude and directionality information derived ultimately from the employed three-axis accelerometer structure, will be handled conventionally by the clinician/computer "alliance".

In one, important form of the invention, beyond that form which features the use of just a single accelerometer, plural, similar, and similarly attached, accelerometers are employed. This mode is especially useful in relation to capturing the most robust murmur information.

In all instances, given the state of the art today involving the making of extremely tiny mechanical and electromechanical structures, a three-orthogonal-axis accelerometer, hereinafter referred to frequently simply as a three-axis accelerometer, usable in the practice of the present invention might typically have dimensions on the order of about 5×5×2-mms. Such a device might be "stand-alone" in nature, or it might be structured in combination with relevant, appropriate, algorithmically programmed, signal-data-processing and recording micro-circuitry, either "structural approach", of course, coming with appropriate, readily externally accessible, signal-output connection structure(s). It will be immediately apparent to those skilled in the art that such an accelerometer, as well as all, appropriate signal-data-processing circuitry, including digital computer data-processing and recording circuitry, and algorithmic methodology (as such are described functionally and organizationally below both in high-level text and in block/schematic drawing form) needed to implement the data-handling and result-assessing aspects of the invention, may be conventional in nature, and may take on a number of different, entirely adequate forms. The details of these matters do not form any part of the present invention, and they are, accordingly, not discussed or elaborated herein in great detail. Rather, they are mentioned in the practice of the invention, as just suggested, in appropriate, high-level disclosure terms.

Useful background information regarding such data-processing and algorithmic circuitry and methodology employing digital computer structure, may be found in the following documents, the entire contents of which are hereby incorporated herein by reference: U.S. Pat. No. 7,096,060 to Arand et al., issued Aug. 22, 2006, for "Method and System for Detection of Heart Sounds"; and U.S. Patent Application Publication No. 2007/0191725 of Nelson, published Aug. 16, 2007, for "Wavelet Transform and Pattern Recognition Method for Heart Sound Analysis". Signal-processing algorithmic methodology described in these documents may be employed very satisfactorily in the signal-processing environment associated with practice of the present invention. This point is reiterated later herein in a discussion specifically describing acquired-signal data processing.

Continuing, the method of the invention recognizes that three-dimensional vector sound-based (heart sound and murmur) information, which is contained collectively in all three of the traditional, three, orthogonal axes of anatomical information that may be obtained from a stably positioned, externally anatomically-attached, three-axis accelerometer, is definitively more than that which is traditionally obtained/obtainable from a single-axis (very common), or even a dual-axis (not very common) approach, and that this caliber of information offers a new and powerful route toward developing a convincing, enhancedly-detailed and reliable, assessment of a person's hemodynamic condition. In this regard, the present invention leads an important departure from the years-long lesser approaches that are principally reliant on only single-axis information.

In the field of this invention, and describing a certain, well-known background context, mechanical (heart-valve) events and abnormal fluid dynamics during the cardiac cycle generate specific sounds—heart sounds and murmur (referred to herein as sound-based information, or phenomena)—which can be auscultated and/or detected through mechanical sensors systems placed in contact with the human chest. The temporal and frequency aspects of those phenomena is very specific (a) to each of the different heart sound types (S1, S2, S3, and S4), also referred to herein as heart sounds, and as heart sound components (certain ones of which components includes each a pair of ventricle-specific, left-side and right-side sub-components), and (b) to murmur.

Regarding murmur, or murmurs, conceptually, murmurs are classified as (1) "inflow tract" murmurs of the left side of the heart; (2) "outflow tract" murmurs of the left side of the heart; (3) "inflow tract" murmurs of the right side of the heart; (4) "outflow tract" murmurs of the right side of the heart; and (5) murmurs produced at the site of any left-to-right shunt. In terms of the practice of the present invention, while, according to the preferred form of the invention, very useful vector information regarding such murmurs, or simply, collectively "murmur", can be obtained using a single, three-axis accelerometer stably positioned on the chest, it will in some instances be more useful to employ two or more accelerometers suitably stably anchored to the chest at appropriately spaced locations to pin-point this phenomenon.

Murmur information, as compared with heart sound information, may be collected, to some extent effectively, by a single, three-axis accelerometer placed at one of the precordial, ECG anatomical sites known as V3 and V4, and preferably at the V4 site. but it is much more effectively, and clearly identifiably, collected by plural such accelerometers place at several (below identified) sites which are among the recognized traditional auscultation sites. The present invention proposes different practice modes and system arrangements which differentially recognize these two situations.

The predominantly low frequency characteristic of heart sounds (particularly), and to some extent of murmur, leads to the fact that the wave propagation from their originating sites in the heart to the chest, particularly in the cases of the several, recognized heart sounds, is not solely longitudinal, but more transversal of nature, with propagation speeds in the 1-10-meters-per-second range. One could describe them as being like "ocean waves reaching the shore", in the sense that not every part of the sound wave fronts will reach the surface (the chest) at the same time. As a result, there is a measurable magnitude and phase difference, even between two locations in very close proximity to each other on the chest, which can be registered through mechanical sensor systems. Furthermore, it means that at a single chest location, classic heart sound detection systems, i.e. stethoscopes, microphones or single-axis accelerometers, will pick up only the sound energy component that is perpendicular (i.e., the z-axis, normal vector component) to the chest surface.

However, by using a stably positioned, three-orthogonal-axis accelerometer as proposed here by the present invention, a heart sound and murmur sensor system can also measure accurately the existing, sound-based, heart sound and murmur components occurring within the chest plane (i.e., along the x-axis and the y-axis). Especially, using such a three-axis accelerometer, a resolved, spatial vector, derived from acquired, three-dimensional sound components that are associated with the traveling wave of a particular sound-phenomenon, can be constructed and associated with appropriately band-pass-filtered frequency information, whereby:

(a) the magnitude (amplitude) of such a vector will provide information regarding the associated heart-source-based wave energy level, and (b) the filtered signal frequency information, coupled with (c) the determined angle of the derived spatial vector, obtained from a spatial resolution of the individual vector components lying along the orthogonal x, y, and z axes adjacent the stable site of the accelerometer which will furnish information regarding the wave travel direction, will collectively provide accurate data regarding the specific internal heart-valve source of the detected sound-phenomenon (heart sound component, heart sound subcomponent(s), and/or murmur).

To emphasize a significant point, such angular and filtered-frequency information, coming, as it will, ultimately from one or more positionally stabilized, external accelerometer(s), will lead toward a confident identification of the specific internal source (heart valve) of origin of the vector-detected wave. This confident source identification, enhanced, of course, where two or more positionally stabilized external accelerometers are contributors to final data, coupled with both (1) energy-level and (2) "within-the-cardiac-cycle" time-positioning data, is a decided advantage over the prior art offered by the present invention in relation to assisting in the professional, clinical assessment of a subject's hemodynamic condition.

Additionally the temporal variation of three-axis, vector magnitude and/or direction can be used to enhance the detection and classification of heart sounds in computerized systems, as well as the diagnostic and prognostic utility (hemodynamic-condition assessment) in the management of cardiovascular disease states.

Further discussing the relevant field of the present invention, classic auscultation of heart sounds and murmurs are performed with a stethoscope applied to the patient's chest wall. The sounds audible through such stethoscopes are generated by specific temporal conditions of the heart valves, and by temporal aspects of the fluid dynamics during the filling of the ventricles in the cardiac cycle. There are three principle types of sounds, or sound components, generated and detectable through a stethoscope: (1) closure sounds (S1-left-ventricle and S2-right-ventricle—each of these having two sub-components, i.e. subcomponents originating, respectively, from the left side and the right side of the heart); (2) murmurs during the pumping (systole) and/or filling (diastole) cycle in the presence of deteriorating or defective heart valves; and (3) diastolic heart sounds (S3, S4) under abnormal filling conditions. The S1-left-ventricle sound subcomponents come, respectively, from the Mitral and Aortic valves, and the S2-right-ventricle subcomponents come, respectively, from the Tricuspid and Pulmonary valves. Each of these sound phenomena occurs in a different part of the cardiac cycle with, inter alia, a different time-frequency fingerprint. The phrase "time-frequency" used herein refers to the phenomenon that the frequency, or frequency "fingerprint", of a particular heart-produced sound may change and have different values at different times.

In relation to conventional auscultation, there is a well known form of this practice featuring a pattern of plural, data-collection (sound-listening), auscultation sites. A typical "plurality" pattern might include either four ("classic"), or seven ("expanded"), recognized, auscultation locations as follows:

Classic
1. Aortic region. The region between the 2nd and 3rd intercostal spaces at the right sternal border (RUSB—right upper sternal border).
2. Pulmonic region. The region between the 2nd and 3rd intercostal spaces at the left sternal border) (LUSB—left upper sternal border).
3. Tricuspid region. The region between the 3rd, 4th, 5th, and 6th intercostal spaces at the left sternal border) (LLSB—left lower sternal border).
4. Mitral region. The region near the apex of the heart between the 5th and 6th intercostal spaces in the midclavicular line) (apex of the heart).

Expanded*
1. Left Ventricular Area. The area centering on the apex beat, and extending to the fourth and fifth left interspaces, 2-cm. medial to the apex and laterally to the anterior axillary line. In isolated left ventricular enlargement, this area would extend medially, whilst in right ventricular enlargement it would extend laterally.
2. Right Ventricular Area. The area formed by the lower half of the sternum and the fourth and fifth left and right interspaces extending to about 2-cm. from the sternal edge. In conditions with right ventricular enlargement, this area may extend laterally, reaching the point of maximal impulse (clinical apex beat).
3. Left Atrial Area. The area located at the level of the angle of the scapula to the left of the vertebral margin and extending to the posterior axillary line.
4. Right Atrial Area. The area located at the fourth and fifth right interspaces at the right of the sternum, extending for a varying distance, at times to the right mid-clavicular line. In patients with extreme enlargement, it may extend further to the right.
5. Aortic Area. The area formed by the third, left interspace near the sternal edge, and extending across the manubrium to the first, second and third right interspaces near the sternal margin. It may include the right sternoclavicular joint, and often the suprasternal notch.
6. Pulmonary Area. The area formed by the second, left interspace near the sternal edge, extending upwards to the first, left interspace below the clavicle, and to the left sternoclavicular joint, and downwards to the third, left interspace near the sternal margin. This area may also extend posteriorly at the level of the fourth and fifth dorsal vertebrae about 2- to about 3-cm. on either side.
7. Area for Descending Thoracic Aorta. The area located over the dorsal spine (from the second to the tenth dorsal vertebrae) extending about 2- to about 3-cm. to the left of the spine.
*(Reference: P. M. Shah, S. J. Slodki, A. A. Luisada, "A revision of the "classic" areas of auscultation of the heart: A physiologic approach", Volume 36, Issue 2, Pages 293-300, February 1964).

Due to the relative low-frequency nature of the subject heart-produced sounds, their propagation mechanism inside the chest is not solely longitudinal, but rather, and/or also, transversal. While the related, complex, heart-produced "sound waves" are described as "sound", the relevant signal content, which resides in a very low-frequency range, are often registered each as being more a vibration than a sound. The well known heart sounds lie in the range of about 5-Hz to about 125-Hz. Murmur sounds lie in the range of about 75-Hz to about 1.5-kHz.

Therefore, three-axis accelerometers, which are not constrained to the audible range of frequencies, are very suitable for information-acquisition purposes. A stethoscope, mechanical or electronic, picks up the nominal, single-axis component of this complex impulse wave on the chest wall only, and thus develops only limited information. Of course, this quite limited, stethoscopic-information-gathering approach is essentially what has defined external information-acquisition-for-assessment practice for decades. The present invention changes this in a particularly potent and useful way.

More especially, (a) using a stably, externally anatomically anchored, three-orthogonal-axis accelerometer, (b) constructing a spatial vector out of the three-axis information components that are acquired thereby, (c) then calculating the magnitude and phase relationship of this vector to its components, and additionally (d) using the time-frequency fingerprint of such a vector, one can achieve the following important results:
1. Significant improvement in the detection of heart sounds and murmurs;
2. Clear identification of each heart sound and of murmur with a high degree of specificity as to site of origin;
3. Clear identification of each heart sound subcomponent; and
4. As a consequence of these above, three things, a significant advance in supporting the making of a reliable and detailed assessment of a person's (a subject's) hemodynamic condition.

In this setting, the invention may be described, broadly, as a vector method and associated systemic structure for monitoring a subject's hemodynamic condition including (1) attaching a three-orthogonal-axis accelerometer in a stable position externally to a subject's anatomy, (2) during at least one cardiac cycle of the subject, collecting signal data from the so attached accelerometer, (3) processing such collected data to obtain associated vector magnitude and directionality information, and (4) analyzing such vector magnitude and directionality information for assessment of the subject's hemodynamic condition.

A modification of this method takes the form of employing, instead of just one, a pattern of plural, anatomy-attached, three-axis accelerometers to perform the collecting step.

Additionally, the method of the invention contemplates, a bit more specifically, that the analyzing step will include using obtained signal vector information to identify the presences of at least one of (a) a specific heart sound component and its subcomponent, and (b) murmur.

Yet a further way of expressing a mode of practicing the invention is that it may involve using obtained vector information to identify the presences of at least one of (a) a specific heart sound component and its subcomponents, and (b) murmur.

The proposed method also involves, as a further implementation, performing the collecting, processing and analyzing steps over a selected time interval involving plural cardiac cycles to obtain temporal information regarding the subject's heart hemodynamic condition. This temporal information may include very useful indications respecting a subject's hemodynamic condition as indicated by changes over time in signal magnitudes and vector directions.

Regarding each and all of the above ways of describing the methodologic features of the invention, an additional consideration which characterizes yet another linked and modified manner for its practice is one wherein the mentioned processing includes, additionally, obtaining signal time-frequency information and relating this to specific signal vector, magnitude and directionality information.

These and other features and advantages of the present invention will become more fully apparent as the detailed description of it which now follows is read in conjunction with the accompanying drawings.

DESCRIPTIONS OF THE DRAWINGS

FIG. 1 is a stylized, schematic illustration picturing an anatomical setting with respect to which the methodology of the present invention may be practiced. In particular, FIG. 1 pictures two, different, broad-level implementations, or modifications, of the invention. In one of these implementations, a single, three-axis accelerometer is attached at an appropriate, stabilized anatomical location to the outside of the anatomy. In this case of a using a single accelerometer only, it will preferably be placed in one of the so-called "precordial" ECG positions, V3 or V4—locations which are well known to someone skilled in the art of ECG recordings—locations which are close to the apex of the heart. The V4 site is the preferable site.

In the other implementation, plural, three-axis accelerometers are so attached, at spaced, different locations (three, additional, representative locations are marked in the figure) on the anatomy, with these other locations simply being represented by small, darkened cross marks. These three other locations, together with the location illustrated for the pictured accelerometer use, will preferably be, in this case of plural-accelerometer use, one each of the above-identified, classic auscultation locations. The marks resented in FIG. 1 for showing these three (plural), other, representative, anatomical locations also may be read to be illustrations of associated three-axis accelerometers attached at these locations—a drawing approach which avoids overcluttering of FIG. 1 with repetitive details of such additional accelerometers.

FIG. 1 also shows, using a single, broad and darkened arrow, a conventional multiple-lead ECG connection to the illustrated and labeled chest wall.

Figure 2:
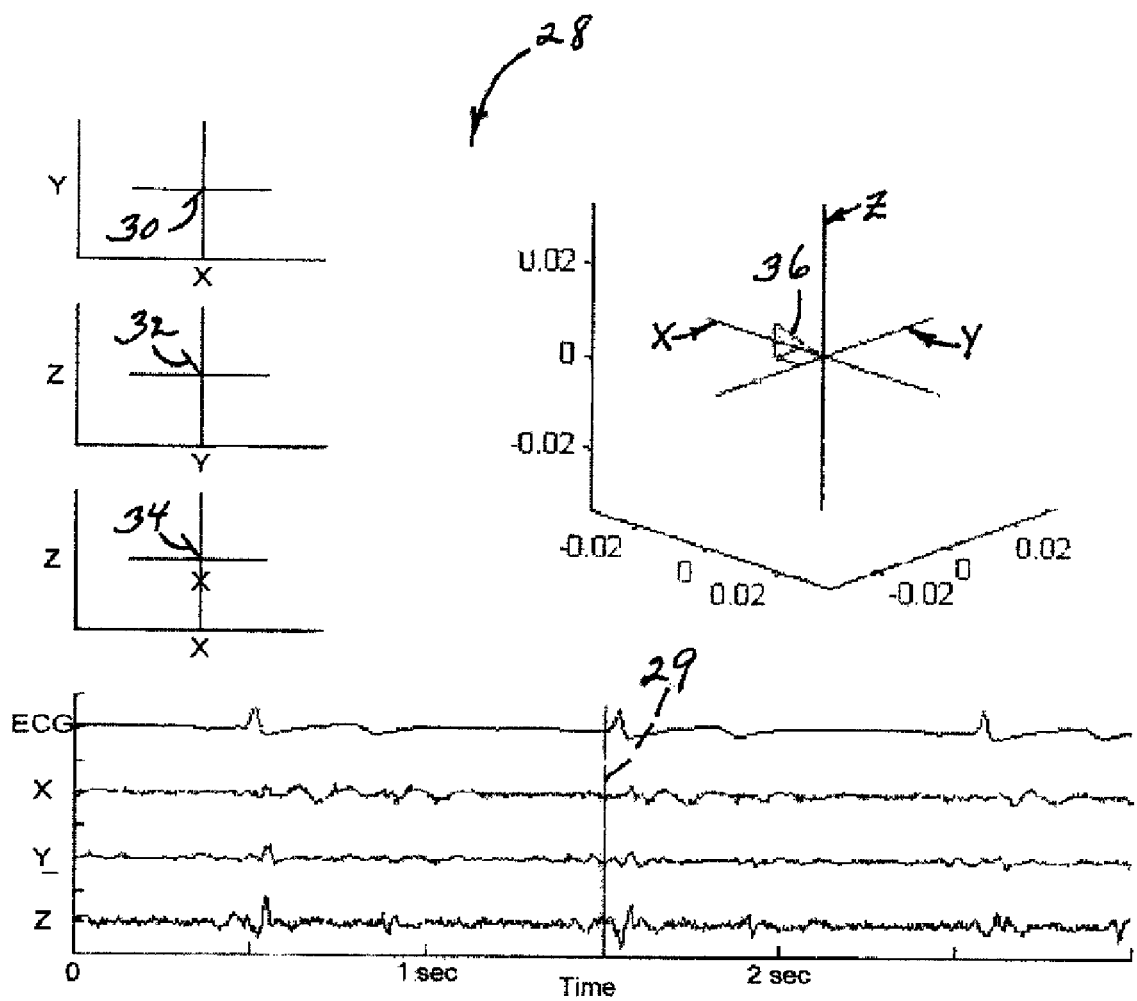

FIG. 2 illustrates, graphically, representative, acquired, both non-spatial and spatial-vector, signal information obtained through collection, and arrived at through certain vector processing, in accordance with practice of the present invention.

In the upper, right portion of this figure, what is presented (in a two-dimensional manner) is a three-dimensional display of one, processed, resultant, three-dimensional, spatial, heart-produced sound vector which relates to a particular, common-time, single-point-in-time, associated, x, y and z accelerometer sound-component acquisitions.

In the upper, left portion of FIG. 2 there appears a vertically organized cluster of three, similar graphs which, moving downwardly through this cluster, furnish projections in the yx, the zy, and the zx planes of the same sound vector shown in the upper, right part of the figure.

In the lower portion of this figure, there are pictured four, time-based traces representing actual recordings of acquired electrical, and band-pass-filtered sound, signals made at a point in time existing within a time period spanning a single cardiac cycle (somewhat more than two such cycles are shown in this figure portion). The uppermost one of these traces is an ECG recording. The lower three traces are of the band-pass filtered x, y and z components of an acquired, three-axis accelerometer signal carrying relevant heart-produced sound information. An evident, vertical-line time marker which crosses all four of these traces indicates the x, y, z signal conditions at a single moment in time that were employed specifically to create the information presented in the upper two portions of FIG. 2.

Understanding that even a single sound event occurring at a single source in the heart may result in the transmission of a sound wave signal which, even at a single accelerometer site, may result in the three orthogonal vectors of that signal arriving out of phase with one another, it is important to recognize that a three-dimensional spatial vector, like that just described above with respect to this drawing figure, which is calculated and constructed in accordance with practice of the present invention, derived from the x, y and z component information arriving at an accelerometer at one particular point in time, will differ from the same kind of resultant vector developed from same-source x, y and z component information arriving at slightly different times. As a consequence, a resultant spatial vector so constructed, viewed over time, will actually move in three-dimensional space, but should always point quite accurately and identifyingly to the source of the originating sound. Those skilled in the art will readily recognize this, and understand how proper interpretation, analysis and assessment should take place.

If desired, of course, it is possible through appropriate and conventional algorithmically controlled signal processing, to acquire, for example, what appear to be the peak x, y and z values of the components of a given sound wave, notwithstanding the out of phase nature of these components, and from this information construct another kind of resultant, three-dimensional, spatial vector which is based upon an artificially created reality that all three "maximum-value" component elements actually arrived at a particular accelerometer at exactly the same point in time.

Figure 3:
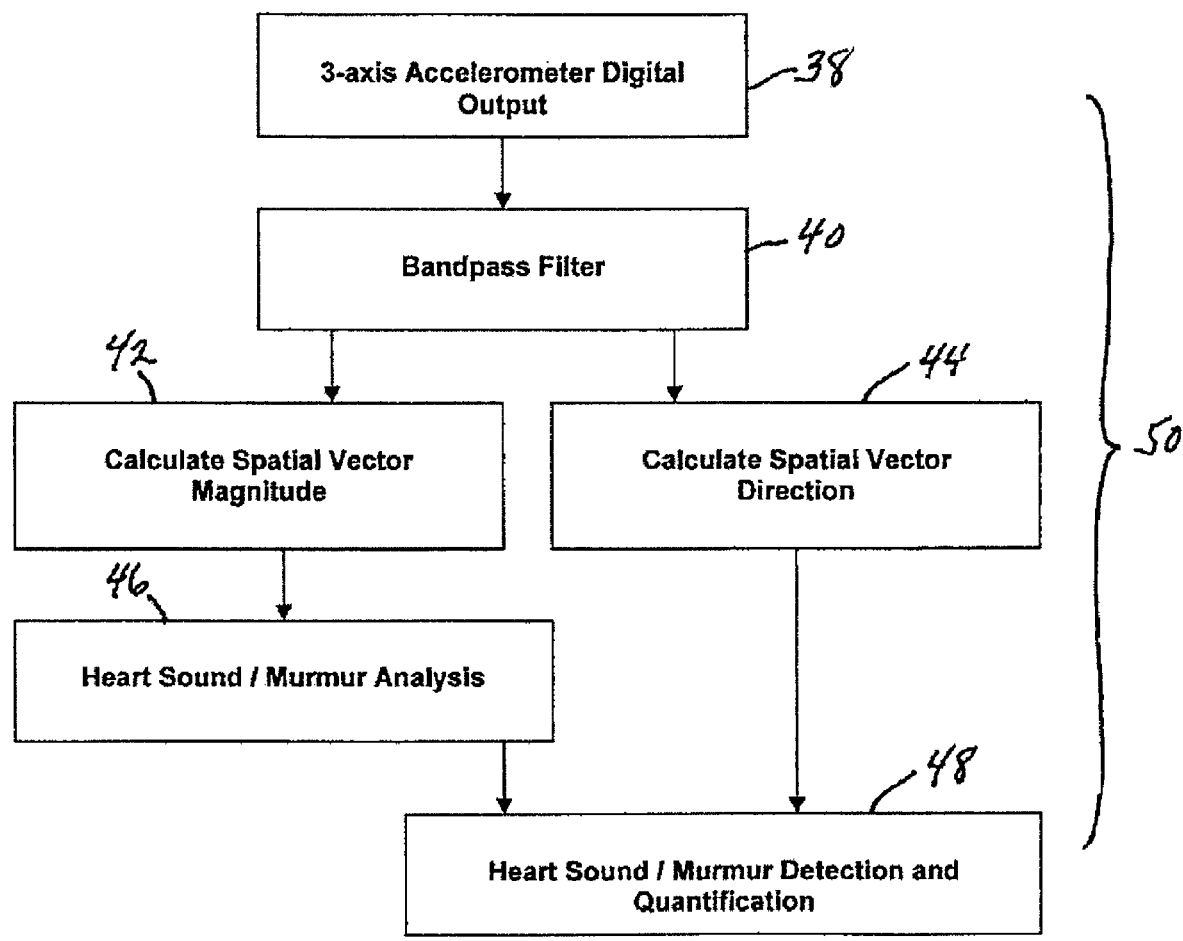

FIG. 3 is a high-level block/schematic diagram illustrating the overall methodology and system of the invention. It is in this figure that high-level functional labeling provided in the pictured, processing-flow-interconnected functional and structural blocks should be understood to be descriptive of otherwise conventional and known structures, algorithms, signal-processing methodologies, etc., that are usable in the practice of the invention. It will be understood that what takes place within the functional and structural blocks presented in this figure all links to the key supply of collected heart sound and murmur information flowing from the one or more employed, externally anatomically attached and stably anchored accelerometer(s).

As is true with regard content of FIG. 1, FIGS. 2 and 3 are readable, as will be explained below, to describe a methodologic implementation of each of the two illustrative practice approaches represented in FIG. 1.

DETAILED DESCRIPTION OF THE INVENTION

Turning now to the drawings, and referring first of all to FIG. 1, indicated generally at 10, in a stylized and schematic form, and without any particular attention paid to the scales in which things in this figure are shown, is a fragmentary portion of a subject's anatomy, including a portion 12 of the chest wall, inside of which is shown a cut-away, or cut-open, illustration of the heart 14, and outside of which is pictured a conventional, small, three-orthogonal-axis accelerometer 16. Accelerometer 16, as mentioned earlier, may either be a stand-alone device with suitable connection structure (not shown) accessible for connection to external signal-processing structure, such as that which may be incorporated into and with a conventional digital computer (also not shown), or it may be more in the nature of a self-contained device which includes embedded signal-processing and associated algorithmic circuitry, software, etc., again equipped with appropriate, outwardly accessible connection structure that may extend also to an external device such as a conventional digital computer.

Accelerometer 16 is, in accordance with an important feature of the present invention, suitably anchored in a stabilized position on the anatomy so that its orientation, while in relation to external, three-dimensional space might change as determined by subject body motions, will firmly hold its position relative to the anatomy so that signal data from sound phenomenon acquired/detected by the accelerometer will essentially remain spatially, positionally and directionally fixed in relation to the anatomy, and therefore in relation to heart 14. Accelerometer 16 may be stably anchored to the anatomy in the familiar, tenacious manner that the ends of ECG leads are so anchored.

Specifically, accelerometer 16 will first be described as being disposed, as pictured in FIG. 1, in the above mentioned, preferred, precordial, ECG V4 site on the subject's chest, wherein it will function, in one of the modes of implementation of the invention the present invention, as a singular accelerometer to collect all heart-produced sound data. Accordingly, FIG. 1, as well as still-to-be-discussed FIGS. 2 and 3, should now be read initially as having a particular focused relevance just to such a single-accelerometer approach, and namely to one specifically linked to accelerometer 16 functioning individually.

However, before progressing with such a single-accelerometer focus, we continue here first with a mention of other things that are shown in FIG. 1. Accordingly, additionally presented schematically in this figure is a representative pattern of plural accelerometers, wherein the accelerometers in this pattern, other than accelerometer 16 which forms part of the pattern, are not specifically shown. In this pattern, accelerometer 16 should be considered to be placed at a location on the subject's chest which is different from the above-mentioned V4 site, and more specifically at one of the four, earlier-identified, "classic" auscultation sites, with, three other, like-constructed three-axis accelerometers, similarly anchored in stable positions on the anatomy, at the other three, "classic" auscultation sites. These three other accelerometers are represented by small darkened cross marks 18, 20, 22 in FIG. 1.

It should be understood that where plural accelerometers are to be used, the number employed is not necessarily four, but rather might be just two, or up to, say, seven.

As can be seen in the FIG. 1, cut-open illustration of heart 14, the four (in total), left-side and right-side valves (two per side) in the heart are clearly pictured and are text-labeled in this figure. Also shown in FIG. 1 are two sound-phenomenon waves represented at 24, 26, emanating, respectively, from the regions of the Mitral valve and the Aortic valve, respectively. It should be understood that, in the description of the present invention, these two waves may be viewed as being representative of heart-produced sound phenomena which may either relate directly to a particular heart sound and to its subcomponents, and/or to murmur. While these waves have been pictured in FIG. 1 relatively specifically traveling toward the location of accelerometer 16, it will be apparent that these very same waves also travel toward the three other accelerometer sites 18, 20 and 22.

For various, well known timing and cardiac-cycle, heart-action confirmation purposes, and in support of practice of the present invention, ECG data is collected in a conventional manner using any appropriate ECG lead structure. This arrangement is represented by a single, broad, darkened arrow 27 in FIG. 1. The ECG connection to the anatomy is preferably made to either the recognized V3 or the V4 site.

It will become quite evident to those skilled in the art, that almost only by simply viewing the content of FIG. 1 in the drawings, coupled with making a careful reading of the above-described features and step practices of the present invention, one will know exactly how to implement and practice the present invention. FIGS. 2 and 3, and comments made about them below, additionally securely anchor this invention-understanding position.

As was mentioned earlier herein, circuitry, such as digital computer circuitry, and algorithmic methodology, which may collaboratively be provided and employed (in well known ways and with well known structures, and substructures) to process positionally reliable (i.e., positionally stably acquired) three-dimensional vector data obtained by collection from the one or more employed accelerometers, can function conventionally to provide, for a clinician's professional assessment of a subject's hemodynamic condition, aided by an allied digital computer properly conventionally programmed, clearly confirmedly detected, and plainly source-identified, heart sound and murmur magnitude, timing and directionality information. It is for this reason that the drawing illustrations, and the modal descriptions of the present invention furnished in the herein detailed-description text, are presented at what is referred to herein as a high-level—one which is specifically designed to set a clear stage for establishing a solid understanding by those skilled in the art of the several, key, preferred and best-mode ways described herein in which to practice the invention.

Centrally important to the invention, and not at all conventional, is the fact that external, three-axis, positionally stably anatomically-anchored accelerometers, or a single such accelerometer, are(is) used for the acquisition and vector presentation of heart-produced sound information. It is based upon this central concept that a significantly enhanced, processed-data foundation is provided to the professional clinician for hemodynamic condition assessment.

FIG. 2 in the drawings should now be read along and in conjunction with what is illustrated, and what has just been described with respect to, FIG. 1. What is shown specifically in FIG. 2, generally at 28, is a three-portion illustration of vector and signal-trace information representing, for example, sound signal information received by accelerometer number 16. This information has been appropriately processed, including band-pass filtered, to identify three-axis, orthogonal x, y, z components of a received, heart-produced sound wave, such as sound wave 24. These three orthogonal components have been resolved into a resultant, three-dimensional, spatial vector which gives important "wave-24" magnitude and directional information, in existence at a particular point in time which has been marked by a vertical line at 29 in the lower portion of this figure—a point in time which lies within a given cardiac cycle, in accordance with practice of the present invention. Line 29 may be viewed as having been placed at a point in time which is just before, or perhaps slightly into the beginning of, an occurrence of the first heart sound S1.

More specifically, the three-pictorial cluster of graphical presentations appearing adjacent the upper left corner of FIG. 2 represents, from top-to-bottom, and at the time marked by line 29, three, two-axis projections—30 in the yx plane, 32 in the zy plane, and 34 in the zx plane—of the earlier mentioned, resultant, three-dimensional, spatial sound vector, here shown and numerically identified at 36 in the upper, right part of FIG. 2. As was also mentioned earlier, this sound data information vector relates illustratively to wave 24.

The resultant vector, 36, is calculated in a conventional manner, as by a suitably programmed digital computer (not shown), with such calculation yielding the important magnitude and direction information relating to representative wave 24 as detected by accelerometer 16 at time 29. Recognizing that this spatial vector, and it magnitude and directionality information, relate to but a single point in time, and recalling the wave-component phase discussion presented above, it will be evident that, in the practice of the invention, the generation of closely time-successive, following spatial vectors with their respective magnitude and directionality informations will furnish deeply confirming, and valuable hemodynamic-condition-assessment-aiding, information about the sound event (probably S1) which has sourced them.

It is this kind of vector information, collected by an accelerometer, such as accelerometer 16, which may be combined with that associated with plural, other, heart-produced sound-wave events which occur over a selected time interval spanning at least a single cardiac cycle, regarding which further conventional processing may be performed, including appropriate band-pass frequency filtering, to provide the character of reliable, useful information which may be employed readily and confidently, i.e., with respect for a great deal of accuracy, by a professional clinician to assess a subject's hemodynamic condition. Accuracy, related to the ability which is furnished by practice of the present invention to pinpoint the source location of each particular wave, is greatly enhanced by the fact that this invention involves the use of one or more external accelerometers anchored in very stable positions on the outside of a subject's anatomy.

This "accelerometer-stability-founded" kind of accuracy, and especially the enhanced accuracy which may come from the employment of plural, external, positionally stabilized accelerometers, sharply distinguishes the character of hemodynamic-condition assessment-supporting data which is received from externally collected information from that which might be acquired by a typical internal, or implanted accelerometer whose singularity, and positional instability (due to what is often known as a subject "fiddle factor"—i.e., externally manipulating the spatial disposition of an internally implanted medical device) can introduce instability inaccuracy in acquired and processed data.

The lower, four signal traces which appear at the bottom side of FIG. 2 furnish representations of the actual traces of collected, and preferably recorded, ECG data, and x, y, and z vector components derived from an accelerometer, such as accelerometer 16. ECG information is usefully obtained from a suitable application to the anatomy (see 27 in FIG. 1) of a conventional ECG lead set for collecting this category of information which helps to provide time marking for events that are sound-based in nature, and also, and to some extent, to provide confirmatory information with respect to identifications of various ones of the heart-produced sounds.

FIG. 3 in the drawings furnishes a clearly laid out and essentially self-explanatory block/schematic diagram which illustrates practice of the present invention. In particular, this figure illustrates the acquisition and processing flow of three-orthogonal-axis accelerometer acquired data. The six blocks which appear in this figure, indicated at 38, 40, 42, 44, 46, 48 are plainly labeled to describe the nature of signal and data handling which takes place within these blocks. Blocks 40, 42, 44, 46, 48 are also referred to herein as substructures of system computer structure (mentioned immediately below), providing, and appropriately named in relation to, specific data-processing functions that are discussed below. Also shown representatively in FIG. 3, by a tall, vertical bracket 50 which appears adjacent the right side of this figure, is a suitably algorithmically programmed digital computer, or digital computer circuitry having data storage capability. This structure may be independent of accelerometer structure, or as mentioned earlier, may be integrated with it. The arrow which extends from block 38 to block 40 may be thought of as being an operative connection existing between the accelerometer structure and the programmed, digital computer data-processing structure, in existence when the system of the invention is in an operative condition relative to a person's anatomy. Other block-interconnecting arrows in FIG. 3 illustrate other, relevant, inter-substructure operative connections.

The following general description, linked with the understanding, discussed above, that what takes place within the blocks pictured in FIG. 3, and what structures and algorithms are or may be involved relative to these blocks (here, note the two, prior-art documents that are identified above and incorporated in this disclosure by reference), are conventional, will clearly explain to those skilled in the art the methodologic practice of the present invention.

Recalling that lying at the heart of the present invention are the foundation steps of (1) attaching a three-orthogonal-axis accelerometer in a stable position externally to a subject's anatomy, during at least one cardiac cycle of that subject, (2) collecting signal data from the so attached accelerometer, and then (3) processing such collected data to obtain associated vector magnitude and directionality information, and (4) analyzing such vector magnitude and directionality information for assessment of the subject's hemodynamic condition, it will be apparent that the details of the last, two, just-stated steps of the invention, beyond the accelerometer attachment and signal collection steps, are performed by blocks 40, 42, 44, 46, 48 pictured in FIG. 3, up to the point where analyzing and assessing takes place—a practice which is implemented, aided by a suitably programmed digital computer, through the knowledge and skill of someone skilled in the art, such as a skilled medical clinician. Where practice of the invention involves the use of plural, spatially-anatomically-placed, three-orthogonal-axis accelerometers, for example to enhance data acquisition relevant to detecting, for assessment, heart murmur, the various processing, etc. steps now discussed below in relation to a single accelerometer are performed collaboratively, and understandably, in association with such plural accelerometers.

Thus, block 38 represents at least one externally stably positionally attached accelerometer, such as accelerometer 16, from which three-axis, sound-based, heart-generated, vector signal data is received and furnished to block 40, wherein appropriate band-pass filtering is applied, in accordance with the band-pass frequency ranges mentioned earlier herein, to isolate and generally identify only that accelerometer data which is most likely to relate to a heart-produced sound, such as one of the classically recognized heart sounds, and/or murmur. Band-pass vector information developed in block 40 (by computer circuitry 50) flows next to blocks 42, 44, as shown, wherein certain vector signal data processing and calculating takes place.

The calculations which occur within blocks 42 and 44 preferably happen under the control of above-mentioned digital computer 50.

Within block 42, the vector magnitude data which is there calculated will be associated, in accordance with the just previously completed band-pass filtering, to a relevant heart sound component (i.e., heart sound), heart sound subcomponent, or murmur event. Such magnitude information may suitably be stored at this point in any suitable, preferably digital format manner. This magnitude information will result in later assignment, soon-to-be mentioned, of important quantification to various, detected, heart-produced sound events.

The vector directional-calculation results which take place within block 44 to produce three-dimensional spatial vectors, like previously mentioned spatial vector 36, may also be suitably stored, and will assign and link specific spatial directionality information to the different spatial vectors which are calculated, and specifically spatial directionality that will associate these vectors with the companion vector information that has been substantially simultaneously calculated within block 42. This results in appropriate, companion, magnitude and directionality informational association to (a) detected heart sound components specifically, (b) to specific heart sound subcomponents, and/or to (c) murmur events.

These calculations which have just been mentioned that occur within blocks 42, 44 of course take place, in the preferred practice of the invention, in specific relations to different particular points in time within at least one cardiac cycle, or in many instances, at different points in time distributed throughout a plurality of heart cardiac cycles, and even over very long, and even time-spaced (days, weeks, months, etc.), intervals. It will be apparent that the calculations performed in blocks 42, 44 will ultimately be used to furnish information to someone, such as a skilled medical clinician, about exactly positionally to where, and with what magnitude, in a subject's heart (i.e., from which valve within the heart) a particular spatial vector that has been calculated points. It should also be apparent that the assignation of spatial vectors to particular classic heart sounds, to heart sound subcomponents, and to murmur events, will be aided by the availability in the above described calculation environment of companion ECG information which is furnished by previously mentioned ECG connection 27.

Block 46 which receives information from block 42 is actually the processing location wherein spatial vector magnitude information becomes analyzed, or at least (some might differently assert) pre-analyzed, with respect to making clear identifications, including timing information as a factor, respecting the internal source, i.e., the specific heart source, of the origination of a particular sound event, whether that sound event be a specific one of (a) the four classic heart sound components, (b) certain heart sound subcomponents, or (c) a murmur event.

As has been mentioned, the basic practice of the invention, in aid of hemodynamic-condition assessment, may be performed simply within a single cardiac cycle, over a span of several cardiac cycles, or indeed, over relatively longer periods of time to detect changes which may occur in vector magnitude and directionality information respecting related heart sound and murmur events.

Summarizing, then, the invention thus offers a powerful approach aimed at assisting a professional medical clinician in assessing a subject's hemodynamic condition—an approach based centrally upon acquiring, and presenting to such a clinician, stability-characterized vector data collected non-invasively from outside the subject's body through one or more positionally stabilized, three-axis accelerometer(s). Springing from this approach, the finally applied assessment thinking which lies necessarily and ultimately behind one's specifically determining the hemodynamic-condition meanings of acquired and presented vector data, in relation, of course, to determined vector magnitude and directionality information, and vector "time-change" information, is thinking which rests well within the knowledge and skill of those generally skilled in the relevant medical art.

The foundation behavior and practice of the present invention, a behavior which involves data acquisition utilizing anatomically positionally stabilized, external, three-orthogonal-axis accelerometers, or at least one such accelerometer, leads to the development of the kind of analyzable vector data which uniquely arms a professional clinician to make, with a great deal of confidence and reliance on accuracy, a well-data-supported assessment of a subject's hemodynamic condition.

Accordingly, while preferred embodiments and manners of practicing the invention have been described and illustrated herein, and certain variations and modifications suggested, we appreciate that other variations and modifications may be made without departing from the spirit of the invention.

We claim:

1. A plural-external-anatomical site vector method for monitoring, exclusively externally, a subject's hemodynamic condition utilizing, and based upon, exclusively externally collected data relating to murmur and heart sound phenomena, detected by, and collected exclusive from, plural, externally anatomically-attached, stably positioned, three-orthogonal-axis accelerometers, said method comprising
    attaching at least a pair of three-orthogonal-axis accelerometers in stable, spaced positions externally to a subject's anatomy,
    during at least one cardiac cycle of the subject, collecting signal data collaboratively from the so-attached, plural accelerometers,
    processing such collaboratively collected data to obtain vector magnitude and directionality information associated, respectively, with the least two accelerometers, and
    analyzing such collaboratively collected and processed vector magnitude and directionality information for assessment of the subject's hemodynamic condition.

2. The method of claim 1, wherein , respectinq collaborative treatment associated with the at least two accelerometers, said processing involves examining, including frequency filtering, the frequency content of collected data (1) to distinguish heart sound content from murmur content, and (2) to develop vector magnitude and directionality information respectively related to each of these two phenomena, and said analyzing employs all of such respectively developed information.

3. The method of claim 1, wherein said analyzing involves using such obtained vector information to identify the presence of at least one of (a) a specific heart sound component, and (b) murmur.

4. The method of claim 1, wherein said analyzing involves using such obtained vector information to identify the presence of at least one of (a) a specific heart sound component and its subcomponents, and (b) murmur.

5. The method of claim 1 which further comprises performing said collecting, processing, and analyzing steps over a selected time interval involving plural cardiac cycles.

6. The method of claim 1 which further comprises obtaining from the attached, plural accelerometers signal time-frequency information, and said processing and analyzing include relating this time-frequency information to associated, signal vector, magnitude and directionality information.

7. The method of claim 1 which further comprises, during said collecting, acquiring time-related ECG data.

8. The method of claim 7, wherein said analyzing involves using such obtained vector information to identify the presence of at least one of (a) a specific heart sound component, and (b) murmur.

9. The method of claim 7, wherein said analyzing involves using such obtained vector information to identify the presence of at least one of (a) a specific heart sound component and it subcomponents, and (b) murmur.

10. A computer-based system for plural, external-anatomical-site vector monitoring, externally, of a subject's hemodynamic condition utilizing, and based upon, exclusively externally anatomically collected data relating to murmur and heart sound phenomena, detected by, and collected exclusively and collaboratively from, plural, externally anatomically-attached, stably positioned, three-orthogonal-axis accelerometers, said system, when disposed in an operative condition relative to a subject, comprising
    at least a pair of three-orthogonal-axis accelerometers attached, in stable, spaced positions, externally to a subject's anatomy at selected, classically recognized, auscultation sites on the anatomy, and
    signal-data-processing computer structure operatively connected to said accelerometers, possessing appropriate, signal- and data-processing computer substructures, and operable, during at least one cardiac cycle of the subject, to collect for processing, and to process, signal data collaboratively from said at least a pair of anatomy-attached accelerometers, said computer substructures including
    (a) band pass filter substructure substantially directly operatively connected to said accelerometers, operable to apply appropriate, band-pass frequency filtering both of (1) heart sounds that lie in the range of about 5-Hz to about 125-Hz, and (2) murmur sounds that lie in the range of about 75-Hz to about 1.5-kHz, (b) operatively connected to said band pass filter substructure, and operatively associated with one another, vector-signal-data processing substructures, including (1) spatial vector magnitude-analyzing substructure for analyzing spatial vector magnitude information, and (2) spatial vector directionality analyzing substructure for analyzing spatial vector directionality information, respectively received from said band pass filter substructure, (c) heart-sound and murmur-analysis substructure operatively connected to said spatial vector magnitude-analyzing substructure for performing heart-sound and murmur analysis, and (d) heart-sound and murmur-detection and quantification substructure operatively connected to said heart-sound and murmur-analysis substructure, and to said spatial vector directionality analyzing substructure, for performing heart-sound and murmur-detection and quantification, said computer structure and its included computer substructures this being constructed for analyzing the referred-to vector magnitude and directionality information for assessment, and an aid to assessment, of the subject's hemodynamic condition.

* * * * *